(12) United States Patent
Tang et al.

(10) Patent No.: US 7,617,736 B2
(45) Date of Patent: Nov. 17, 2009

(54) METALLIC THIN FILM PIEZORESISTIVE TRANSDUCTION IN MICROMECHANICAL AND NANOMECHANICAL DEVICES AND ITS APPLICATION IN SELF-SENSING SPM PROBES

(75) Inventors: Hongxing Tang, Pasadena, CA (US); Mo Li, Pasadena, CA (US); Michael L. Roukes, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/164,620

(22) Filed: Jun. 30, 2008

(65) Prior Publication Data

US 2009/0038404 A1    Feb. 12, 2009

Related U.S. Application Data

(63) Continuation of application No. 11/010,578, filed on Dec. 14, 2004, now Pat. No. 7,434,476, and a continuation-in-part of application No. 10/826,007, filed on Apr. 16, 2004, now Pat. No. 7,302,856.

(60) Provisional application No. 60/562,652, filed on Apr. 15, 2004, provisional application No. 60/468,452, filed on May 7, 2003.

(51) Int. Cl.
*G01B 7/16* (2006.01)
(52) U.S. Cl. .......................................... 73/777; 73/760
(58) Field of Classification Search ............ 73/760–777
See application file for complete search history.

(56) References Cited

U.S. PATENT DOCUMENTS

| | | | |
|---|---|---|---|
| 3,034,345 A | 5/1962 | Mason | |
| 4,798,206 A | 1/1989 | Maddison et al. | |
| 5,266,801 A | 11/1993 | Elings et al. | |
| 5,345,816 A | 9/1994 | Clabes et al. | |
| 5,475,318 A | 12/1995 | Marcus et al. | |
| 5,517,280 A | 5/1996 | Quate | |
| 5,559,330 A | 9/1996 | Murashita | |
| 5,619,139 A | 4/1997 | Holczer et al. | |
| 5,666,190 A | 9/1997 | Quate et al. | |
| 5,672,816 A | 9/1997 | Park et al. | |
| 5,831,181 A | 11/1998 | Majumdar et al. | |
| 5,856,672 A | 1/1999 | Ried | |

(Continued)

FOREIGN PATENT DOCUMENTS

WO    WO 03/095616 A2    11/2003

(Continued)

OTHER PUBLICATIONS

Harley et al., "High-Sensitivity Piezoresistive Cantilevers Under 1000 A Thick," Applied Physics Letters, vol. 75, No. 2, American Institute of Physics, Jul. 12, 1999, pp. 289-291.

(Continued)

*Primary Examiner*—Max Noori
(74) *Attorney, Agent, or Firm*—Foley & Lardner LLP

(57) ABSTRACT

Thin metallic films are used as the piezoresistive self-sensing element in microelectromechanical and nanoelectromechanical systems. The specific application to AFM probes is demonstrated.

20 Claims, 13 Drawing Sheets

U.S. PATENT DOCUMENTS

| | | | |
|---|---|---|---|
| 5,883,705 | A | 3/1999 | Minne et al. |
| 5,939,623 | A | 8/1999 | Muramatsu et al. |
| 6,000,947 | A | 12/1999 | Minne et al. |
| 6,006,606 | A | 12/1999 | Shinogi et al. |
| 6,075,585 | A | 6/2000 | Minne et al. |
| 6,185,991 | B1 | 2/2001 | Hong et al. |
| 6,784,074 | B2 | 8/2004 | Shchukin et al. |
| 6,823,717 | B2 | 11/2004 | Porter et al. |
| 6,823,724 | B1 | 11/2004 | Kobayashi et al. |
| 6,851,301 | B2 | 2/2005 | Kim et al. |
| 6,882,051 | B2 | 4/2005 | Majumdar et al. |
| 6,887,365 | B2 | 5/2005 | Naughton |
| 6,945,099 | B1 | 9/2005 | Su et al. |
| 6,967,362 | B2 * | 11/2005 | Nam et al. ............... 257/254 |
| 7,041,963 | B2 | 5/2006 | El Rifai et al. |
| 7,159,448 | B2 * | 1/2007 | Moelkner et al. ......... 73/35.12 |
| 7,302,856 | B2 | 12/2007 | Tang |
| 7,420,320 | B2 * | 9/2008 | Sano et al. ................ 310/363 |
| 2002/0166962 | A1 | 11/2002 | Roukes et al. |
| 2002/0174715 | A1 | 11/2002 | Kim et al. |
| 2002/0178801 | A1 | 12/2002 | Takahashi et al. |
| 2003/0062193 | A1 | 4/2003 | Thaysen et al. |
| 2003/0089182 | A1 | 5/2003 | Thaysen et al. |
| 2003/0135971 | A1 | 7/2003 | Liberman et al. |
| 2003/0142597 | A1 | 7/2003 | Park et al. |
| 2003/0173864 | A1 | 9/2003 | Zalalutdinov et al. |
| 2004/0105560 | A1 | 6/2004 | Naniki |
| 2004/0147132 | A1 * | 7/2004 | Nam et al. ................ 438/720 |
| 2005/0034529 | A1 * | 2/2005 | Tang et al. ................... 73/777 |
| 2005/0109925 | A1 | 5/2005 | El Rifai et al. |
| 2005/0150280 | A1 | 7/2005 | Tang et al. |
| 2005/0164236 | A1 * | 7/2005 | Su et al. ...................... 435/6 |
| 2005/0212529 | A1 | 9/2005 | Huang et al. |
| 2005/0214803 | A1 | 9/2005 | Wang |
| 2005/0236357 | A1 | 10/2005 | Bakkers et al. |
| 2005/0244326 | A1 | 11/2005 | Colbert et al. |
| 2005/0275502 | A1 | 12/2005 | Goebel et al. |

FOREIGN PATENT DOCUMENTS

| | | |
|---|---|---|
| WO | WO 03/095617 A2 | 11/2003 |
| WO | WO 2004/041998 A2 | 5/2004 |

OTHER PUBLICATIONS

Harley et al., "1/F Noise Consideration for The Design and Process Optimization of Piezoresistive Cantilevers," Journal of Microelectromechanical Systems, vol. 9, No. 2, IEEE, Jun. 2, 2000, pp. 226-235.

Hutter et al., "Calibration of Atomic-Force Microscope Tips," Rev. Sci. Instrum., vol. 64, No. 7, American Institute of Physics, Jul. 1993, pp. 1868-1873.

Kuczynski, "Effect of Elastic Strain on The Electrical Resistance of Metals," Physical Review, vol. 94, No. 1, Apr. 1, 1954, pp. 61-64.

Li et al., "Thin Gold Film Strain Gauges," J. Vac. Sci. Technol., vol. 12, No. 3, American Vacuum Society, May 1994, pp. 813-819.

Parker et al., "Electrical Resistance-Strain Characteristics of Thin Evaporated Metal Films," Journal of Applied Physics, vol. 34, No. 9, Sep. 1963, pp. 2700-2708.

Physics Web, "Nanoelectromechanical Systems Face The Future," Physics World Magazine, vol. 14, Issue 2, Feb. 2001, http://physicsweb.org/article/world/14/2/8.

Reid et al., "6-MHz 2-N/m Piezoresistive Atomic-Force-Microscope Cantilevers With Incisive Tips," Journal of Microelectromechanical Systems, vol. 6, No. 4, IEEE, Dec. 4, 1997, pp. 294-302.

Thaysen et al., "Polymer-Based Stress Sensor With Integrated Readout," Journal of Physics D: Applied Physics, vol. 35, Institute of Physics Publishing Ltd., 2002, pp. 2698-2703.

Tortonese et al., "Atomic Resolution With An Atomic Force Microscope Using Piezoresistive Detection," Applied Physics Letters, vol. 62, No. 8, American Institute of Physics, Feb. 22, 1993, pp. 834-836.

Yang et al., "Monocrystalline Silicon Carbide Nanoelectromechanical Systems," Applied Physics Letters, vol. 78, No. 2, American Institute of Physics, Jan. 8, 2001, pp. 162-164.

Melosh et al., "Ultrahigh-Density Nanowire Lattices and Circuits," Science, Apr. 4, 2003, vol. 300, pp. 112-115.

Hrovat et al., "A characterisation of thick film resistors for strain gauge applications," J. Mater. Sci., 2001, vol. 36, pp. 2679-2689.

Knight et al., "Effect of Structure on the Piezoresistive Properties of Thin Metal Films," J. Vac. Sci. Technol., 6, 706-710,1969.

Chung et al., "Micromachined metal thin-film pressure sensor suitable for batch process," Electronics Letters, Oct. 24, 2002, vol. 38, No. 22, 1344-1346.

Pattabi et al., "A simple strain cell for the measurement of gauge factor of a thin film," Rev. Sci. Inst., Apr. 1999, vol. 70, No. 4, pp. 2074-2075.

Bishay et al., "Applicability of discontinuous palladium films as strain gauges," J. Mater. Sci., 1992, vol. 3, pp. 195-199.

Jen et al., "Piezoresistance characteristics of some magnetic and non-magnetic metal films," J. Magn. Magn. Mater., 2003, vol. 256, pp. 54-62.

McGuire et al., "Anisotropic Magnetoresistance in Ferromagnetic 3d Alloys," IEEE Trans. Mag-11, Jul. 4, 1975, No. 4, pp. 1018-1038.

Rajanna et al., "Pressure transducer with Au—Ni thin-film strain gauges," IEEE Trans. Electron Devices, Mar. 1993, vol. 40, No. 3, pp. 521-524.

Sampath et al., "Behaviour of Bi—Sb alloy thin-film strain gauges," Thin-Solid Films, 1986, 137, pp. 199-205.

Chiriac et al., "Ni—Ag thin films as strain-sensitive materials for peizoresistive sensors," Sensors and Actuators A, 1999, vol. 76, pp. 376-380.

Lei et al., "Thin film thermocouples and strain gauge technologies for engine applications," Sensors and Actuators A, 1998, vol. 65, pp. 187-193.

Guckel et al., "Surface micromachined pressure transducers," Sensors and Actuators A, 1991, vol. 28 (2), pp. 133-146.

Patridge et al., "High-performance planar peizoresistive accelerometer," JMEMS, Mar. 1, 2000, vol. 9, No. 1, pp. 58-66.

Chui et al., "Independent detection of vertical and lateral forces with a sidewall-implanted dual-axis piezoresistive cantilever," Appl. Phys. Lett., Mar. 16, 1998, vol. 72, No. 11, pp. 1388-1390.

Dehe et al., "A piezoresistive GaAs pressure sensor with GaAs/AlGaAs membrane technology," J. Micromech. Microeng., 1995, vol. 5, pp. 139-142.

Hsu et al., "Piezoresistive response induced by piezoelectric charges in n-type GaAs mesa resistors for application in stress transducers," J. Appl. Phys. Jan. 1, 1999, vol. 85, No. 1, pp. 333-340.

Tang et al., "Two-dimensional electron-gas actuation and transduction for GaAs nanoelectromechanical systems," Appl. Phys. Lett. Nov. 11, 2002, vol. 81, No. 20, pp. 3879-3881.

Konczewicz et al., "GaAlAs-Based Micromachined Accelerometer," Phys. Stat. Sol. B, 2001, vol. 223, pp. 593-596.

Bykhovski et al., "Piezoresistive effect in wirtzite n-type GaN," Appl. Phys. Lett. Feb. 5, 1996, vol. 68, No. 6, pp. 818-819.

Gaska et al., Piezoresistive effect in GaN-Aln-GaN structures,: Appl. Phys. Lett., Dec. 29, 1997, vol. 71, No. 26, pp. 3817-3819/.

Gaska et al., "Piezoresistive effect in Aln/GaN short range superlattice structures," J. Appl. Phys. May 1, 1999, vol. 85, No. 9, pp. 6932-6934.

Mosser et al., "Energy shifts due to the local environment of DX centers in $Al_xGa_{1-x}As:Si$," Mater. Sci. Forum, 1994, vols. 143/147, pp. 1117-1122.

Eickhoff et al., "Piezoresistivity of $Al_xGa_{1-x}N/GaN$ heterostructures," J. Appl. Phys. Oct. 1, 2001, vol. 90, No. 7, pp. 3383-3386.

Van Vessem et al., "Rediscovering the Strain Gauge Pressure Sensor," Sensors online, vol. 16, No. 4, 6 pgs, Apr. 1999.

Supplementary European Search Report dated Apr. 17, 2009 in EP Appln. No. 03799772.3, 5 pages.

Database Inspec [Online] The Institution of Electrical Engineers, Stevenage, GB, Inspec No. Available Online: Dec. 5, 2001 (abstract of Hohberger et al., "Magnetotransport in freely suspended two-dimensional electron systems for integrated nanomechanical resonators," XP002522700, Fourteenth International Conference on the Electronic Properties of Two-Dimensional Systems, EP2DS-14, Jul. 30-Aug. 3, 2001, Praha, Czech Republic, vol. 12, No. 1-4, Jan. 2002, pp. 487-490).

Database Inspec [Online] The Institution of Electrical Engineers,Stevenage, GB, Dec. 15, 2000, (abstract of Blick et al., "Magnetotransport measurements on freely suspended two-dimensional electron gases," XP002522701, Database accession No. 6837520, p. 17103, left-hand col., paragraph 1, figure 1A, Physical Review B (Condensed Matter) APS through AIP USA, 62(24):Dec. 15, 2000, pp. 17103-17107.

* cited by examiner

METALLIC THIN FILM PIEZORESISTIVE TRANSDUCTION IN MICROMECHANICAL AND NANOMECHANICAL DEVICES AND ITS APPLICATION IN SELF-SENSING SPM PROBES

CROSS-REFERENCE TO RELATED APPLICATIONS

This application is a continuation of U.S. application Ser. No. 11/010,578, filed Dec. 14, 2004, which is a continuation-in-part of U.S. application Ser. No. 10/826,007 filed Apr. 16, 2004, which claims benefit of priority of U.S. Provisional Application Ser. No. 60/468,452, filed May 7, 2003. This application also claims benefit of priority of U.S. Provisional Application Ser. No. 60/562,652, filed Apr. 15, 2004. All of the above mentioned applications are incorporated herein by reference in their entirety.

The U.S. Government has certain rights in this invention pursuant to Grant No. ECS-0089061, awarded by the National Science Foundation (NSF); Grant No. F49620-02-1-0085, awarded by the United States Air Force Office of Sponsored Research (AFOSR); Grant No. DABT63-98-1-00012 awarded by Defense Advanced Research Projects Agency (DARPA) and Grant No. N00014-02-1-0602, awarded by the United States Navy, Office of Naval Research (ONR).

BACKGROUND OF THE INVENTION

1. Field of the Invention

This invention is related to piezoresistive sensors for micro-electro-mechanical systems (MEMS) and nano-electro-mechanical systems (NEMS).

2. Description of the Prior Art

Piezoresitive displacement detection techniques are attractive in both microelectromechanical and nanoelectromechanical systems (MEMS and NEMS), because they can be fully integrated and are easy to use. Applications include scanning probe microscopy, force and pressure sensors, flow sensors, chemical and biological sensors, and inertial sensors such as accelerometers and motion transducers. Most of these applications use p-type doped silicon layer as the sensing element. Doped silicon has a fairly high gauge factor (20~100), but also high sheet resistance (10 kOhm/square) and therefore a relatively large thermal noise floor. Much higher 1/f noise is also expected in doped silicon due to its low carrier density. Additionally, fabrication processes for semiconducting piezoresistors, such as ion implantation or molecular beam epitaxy, are complicated and expensive. Finally, semiconducting materials are also vulnerable to processing damage. Therefore, they are not suitable for some uses at nanoscale dimensions.

There is an unmet need for a piezoresitive sensing element for microelectromechanical and nanoelectromechanical systems that is more sensitive and easier and cheaper to fabricate.

BRIEF SUMMARY OF THE INVENTION

An embodiment of the invention provides a micro- or nanomechanical device comprising a movable element and a thin metal film used for piezoresistive sensing of a movement of the movable element.

BRIEF DESCRIPTION OF THE DRAWINGS

FIGS. 2 and 3 are resonance response curves for the device of FIG. 1a.

DETAILED DESCRIPTION OF THE INVENTION

Figure 1A:
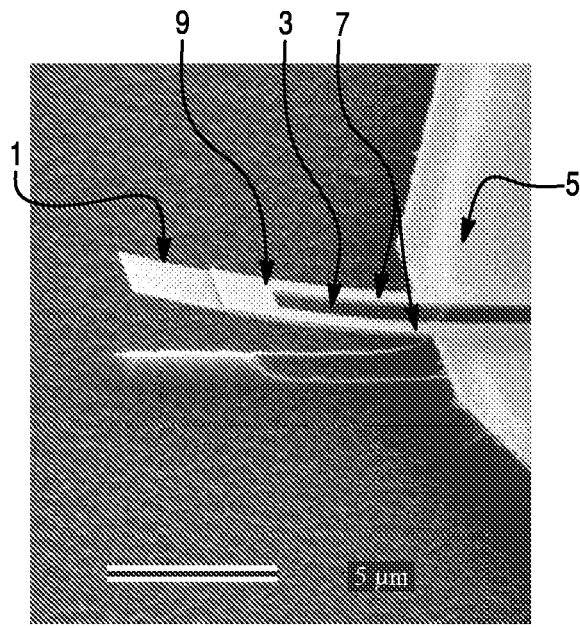
FIGS. 1a and 1b are SEM images of exemplary devices according to embodiments of the invention.

Embodiments of the present invention are directed to metal films used as a piezoresistive self-sensing element in micromechanical and nanomechanical systems. These systems preferably comprise microelectromechanical and nanoelectromechanical systems.

Microelectromechanical and nanoelectromechanical systems include devices with features having a size of 1 micron to 100 microns and 1 nanometer to less than 1 micron, respectively, in at least one dimension, and preferably in two or three dimensions. Preferably, these features comprise movable features or elements, such as cantilevers, diaphragms, clamped beams, wires, etc. Microelectromechanical and nanoelectromechanical systems include, but are not limited to, scanning probe microscopes ("SPM"), such as atomic force microscopes ("AFM"), force and pressure sensors, flow sensors, chemical and biological sensors, and inertial sensors, such as accelerometers and motion transducers. For example, chemical and biological sensors may comprise one or more cantilevers having a surface coated with a material which selectively binds to a chemical or biological analyte (i.e., gas or liquid analyte containing or consisting of the chemical or biological species of interest).

The term "film" includes relatively thin metal films, having a thickness of about 100 nm to about 10 microns, thin metal films, having a thickness of about 10 nm to about 100 nm, and ultra thin metal films, such as discontinuous or island type metal films having a thickness of less than about 10 nm, as will be discussed in more detail below. The term "metal" includes pure or essentially pure metals and metal alloys.

The term "self-sensing" means that the metal film is used as the piezoresistive element without requiring an external motion sensing device, such as a laser which is used to irradiate a cantilever or diaphragm with radiation and a photodetector which is used to detect the reflected radiation to determine the deflection of the cantilever or diaphragm. However, if desired, an external motion sensing device may be used in combination with the self-sensing metal film. Furthermore, the metal film is preferably used with a current source which provides a current across the metal film, and detector which detects the voltage across the metal film to determine the amount (i.e., amplitude, frequency, direction, and/or any other suitable property) of movement of the metal film and movable element.

Strain gauge factor ("gauge factor") is often used to express the electrical resistance and strain relationship of a piezoresistive material, which is defined as $dR/Rd\epsilon=(1+2v)+d\rho/\rho d\epsilon$, where v is Poisson ratio, $\rho$ is resistivity, $\epsilon$ is the strain and R is the resistance. The first term is merely from geometry deformation, and the second term is the physical change of the resistivity due to the change of strain, mainly from strain mediated mean free path in material.

Even though thin metal films have a much lower gauge factor (1~4) than semiconductor piezoresistors, they have much smaller resistance and can bear much higher current density, and therefore yield comparable signal strength. The lower resistance produces less thermal noise. Since metal films have several orders of magnitude higher carrier density than semiconductor piezoresistors, their 1/f noise will be significantly lower. A much lower noise floor makes it possible to obtain similar resolution to silicon devices.

In comparison to semiconducting piezoresistors, metallic thin film piezoresistors can be fabricated at significantly reduced cost. Metal films of thickness from 10 nm to 10 microns can be simply evaporated or sputtered onto almost any substrate, such as Si, SiC, SiN, $SiO_2$, glass and even plastic materials. Processing damages to metal films are minimal. Metal films can be patterned well down to nanoscale dimensions, and batch fabricated onto devices in large arrays.

In a preferred embodiment of the invention, a gold thin film is used for piezoresitive sensing. Those skilled in the art should obtain similar results with other pure or essentially metals including, but not limited to, Ag, Ni, Pt, Al, Cr, Pd, W, and metal alloys such as Constantan, Karma, Isoelastic, Nichrome V, Pt—W, Pt—Cr, etc.

In another preferred embodiment, the metal film is used to coat a movable element, such as a micron (i.e., 1 to 100 microns) or nanometer (i.e., less than 1 micron) size element. The movable element may be any element in a MEMS or NEMS which moves. Preferably, the movable element comprises a flexible, resilient element (i.e., a "flexture"), such as a resonator.

For example, the resonator preferably comprises a micron or nanometer sized cantilever. However, it should be understood that the invention can be used with other resonators, including, but not limited to, doubly clamped beams, torsional resonators, and diaphragm resonators. Non-limiting examples of doubly clamped beam resonators, torsional resonators and diaphragm resonators are disclosed in U.S. patent application Ser. No. 10/826,007, U.S. Pat. No. 6,593,731 and PCT Application PCT/US03/14566 (published as WO/2004/041998) and its counterpart U.S. patent application Ser. No. 10/502,641, all incorporated herein by reference in their entirety. For example, a doubly clamped beam resonator comprises a beam that is fixed on both ends, but whose middle portion is free hanging so that it can flex or move perpendicular to its length. A torsional resonator may comprise, in a non-limiting example, a flexible diamond or polygonal shaped structure mounted at two anchor points and which can move by twisting or turning about an axis between the anchor points, as described and illustrated in U.S. Pat. No. 6,593,731. A diaphragm resonator may comprise any plate shaped resonator which is anchored at one or more edges and whose middle portion is free hanging so that it can move or flex in one or more directions. An example of a diaphragm resonator is a trampoline resonator.

In another preferred embodiment of the invention, the use of thin metallic films as sensors in AFM probes is demonstrated. Processes for fabricating both self-sensing, non-contact/tapping mode piezoresistive SPM probes and sensing contact mode piezoresistive SPM probes are provided. As noted above, the metal film piezoresistive sensing elements can also be used in other MEMS or NEMS devices, such as force and pressure sensors, flow sensors, chemical and biological sensors, and inertial sensors such as accelerometers and motion transducers. The exemplary devices have an estimated displacement sensitivities of at least $1.6\times10^{-6}$/nm and force resolution of at least 3.8 $fN/\sqrt{Hz}$, which is comparable with its doped silicon counterparts, and a noise level below 1 $nV/\sqrt{Hz}$.

Finally, a highly sensitive electronic down mixing readout scheme is employed to extract the piezoresistive response from the thin metal films. In a preferred embodiment, this detection scheme and suitable circuit(s) are used for metallic self-sensing piezoresistive probes for contact mode and non-contact mode AFM operations.

Thin Metallic Films

Thin metal films have a rather low gauge factor (2~4). Because they have much smaller resistance and can bear much higher current density than semiconductor piezoresistors, they can yield comparable signal strength to semiconductor piezoresistors. The lower resistance produces less thermal noise. Since metal films have several orders of magnitude higher carrier density than semiconductor piezoresistors, their 1/f noise will be significantly lower. With devices working at resonant frequency and doing ac measurements, thin metal films can be highly sensitive.

Metallic thin film piezoresistors can be fabricated at significantly reduced cost. Metal films can be simply evaporated or sputtered onto to almost any substrate. Processing damages to metal films are minimal. Metal films can be patterned well down to nanoscale dimensions, and batch fabricated onto devices in large arrays.

In the illustrated embodiment, thin films of gold are used for piezoresistive sensing. For bulk gold, v is 0.42, and the typical gauge factor is 1~4. Thin gold films can be divided into three different regions according to the film thickness. Films with thickness above 100 nm are more bulk like. Films with thickness between 10 nm and 100 nm have a continuous film regime. For a thickness below 10 nm, the film is often discontinuous. Discontinuous film has a much larger strain gauge factor, because of the metal island gap. In the illustrated embodiment, a 30 nm-50 nm thick gold film, which falls into the continuous thin film region, is used as a piezoresistive layer. However, it should be understood that the dimensions of the metallic thin films can vary considerably. For example, based on measurement results, all continuous thin gold films, from 30 nm gold films up to 10 micron film, the piezoresistive response is on the same order of magnitude. The metal film may have any suitable width and length. For example, the metal film may be a narrow wire (such as a wire having a cross sectional area of about 100 $nm^2$ or less) or it may cover all or a portion of a surface of a movable element of the device, and have a width of about 100 nm up to a 10 microns, such as 200 nm to 2 microns.

In addition to gold, a broad group of pure or essentially pure metals, including but not limited to, nickel, platinum, palladium, tungsten, aluminum etc., can also be used for piezoresistive sensing. Metal alloys, including but not limited to, Constantan, Karma, Isoelastic, Nichrome V, Pt—W, and Pd—Cr, can also be used for piezoresistive sensing. The table below lists some of the exemplary metals and the gauge factor for some of these metals.

| Material | Composition | GF |
|---|---|---|
| Au | 100 (i.e., essentially pure or 100% Au), continuous | 2.6 |
| Au | 100, discontinuous | 24-48 |
| W | 100 | |
| Pt | 100 | |
| Al | 100 | |
| Cu | 100 | |
| Cr | 100 | |
| Ag | 100, discontinuous | 45 |
| Pd | 100 | 2.5 |
| Ni | 100 | 40 |
| Constantan | 45 Ni, 55 Cu | 2.1 |
| Nichrome V | 80 Ni, 20 Cr | 2.1 |
| Pt—W | 92 Pt, 8 W | 4.0 |
| Isoelastic | 36 Ni, 8 Cr, 0.8 Mo, 55.5 Fe | 3.6 |
| Karma | 74 Ni, 20 Cr, 3 Al, 3 Fe | 2.0 |
| Ni—Ag | 35-50 Ni, Ag | |
| Pt—Cr | 87 Pt, 13 Cr | |
| Armour D | 70 Fe, 20 Cr, 10 Al | 2.0 |

Resonators

Figure 1B:
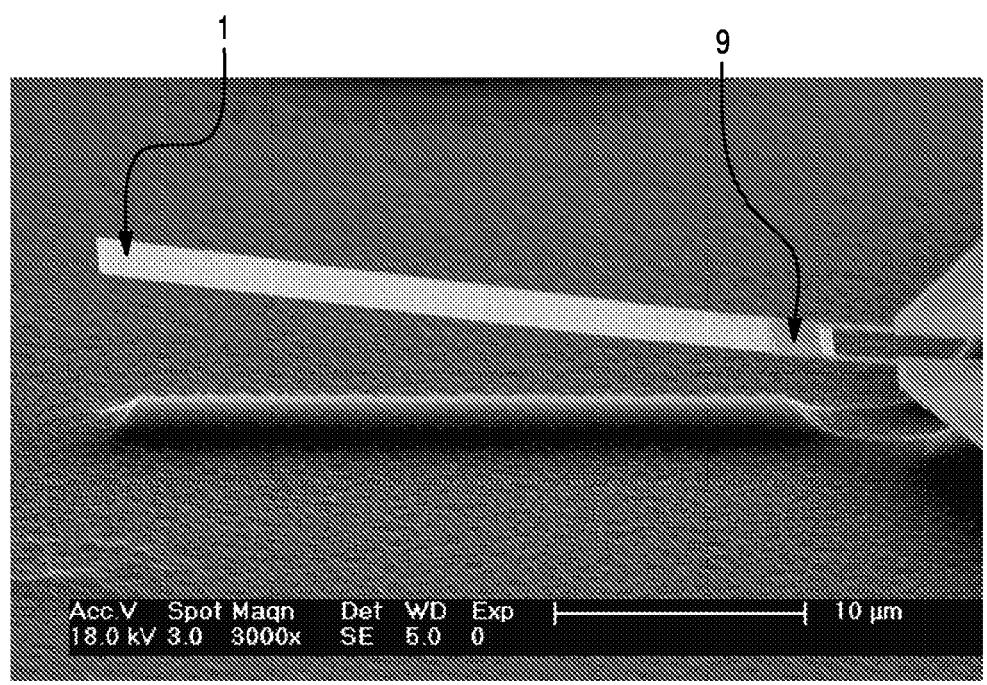

As discussed above, the preferred resonator structures comprise cantilevers, such as cantilvered NEMS or MEMS structures. An SEM image of two exemplary cantilevers are shown in FIGS. 1a and 1b. FIG. 1a is an SEM image of a 10 μm long, 2 μm wide cantilever, with $f_0$=1.5 MHz. FIG. 1b is an SEM image of a 33 μm long, 4 μm wide cantilever, with $f_0$=52 KHz. The devices have a final resistance of 150 ohm. As shown in FIGS. 1a and 1b, the cantilevers 1 preferably contain an opening or notch 3 near the cantilever base 5 containing the contact pads. The portions of the cantilevers 1 which surround the notch 3 are referred to as "legs" 7. The gold film 9 is preferably formed at least in the leg 7 portions of the cantilever. If desired, the notches 3 may be omitted.

Preferably, cantilevered NEMS structures shown in FIGS. 1a and 1b are fabricated using a method similar to that disclosed in Y. T. Yang et al, Appl. Phys. Lett. 78, 162 (2001), incorporated herein by reference. An exemplary method is described below. The starting material is an 80 nm thick epitaxially grown silicon carbide on a silicon wafer. The selection of silicon carbide is more of convenience than of necessity. For example, silicon and its other compounds such as silicon nitride and silicon oxide can be used instead. First, gold contact pads are defined by photolithography. Second, the strain concentration legs, such as the legs 7 shown in FIG. 1a defined by metal interconnection patterns are written by electron beam lithography. A 1 nm chromium adhesion layer followed by a 30 nm gold layer are thermally evaporated on a photoresist pattern located on silicon carbide and then lifted-off to provide a desired pattern. Following ebeam lithography, a 50 nm chromium layer is patterned as an etching mask over the entire cantilever forming area. Then the sample is etched with an electron cyclone reaction (ECR) etcher, using a mixture of 1:1 Ar:NF$_3$ gas. A 250V bias voltage is used to anisotropically etch the SiC layer. The bias voltage is then decreased to 100V, which makes the etching isotropic. A silicon layer below the device cantilever is etched, and the silicon carbide structure is released. Etching is stopped when the cantilever is barely undercut. The chromium mask is removed by wet etch to reduce the stress on the cantilever, which could cause cantilevers to curl up. A final very short ECR dry etch is used to fully release the cantilever. The sample is then glued onto a piezoelectric ceramic (PZT) actuator, and the whole device is mounted onto a chip carrier, and electrical connections are made by wire bonding.

The sample is then loaded into a vacuum tank and measured in room temperature. The measurement system includes a half dc bridge, a battery set as dc bias source and an ac-dc bias tee. The PZT actuator is driven by the output of a network analyzer. After two stages of 67 dB gain, 50Ω input and output impedance preamplifiers, the ac part of the signal is fed back into the network analyzer.

Figure 2:
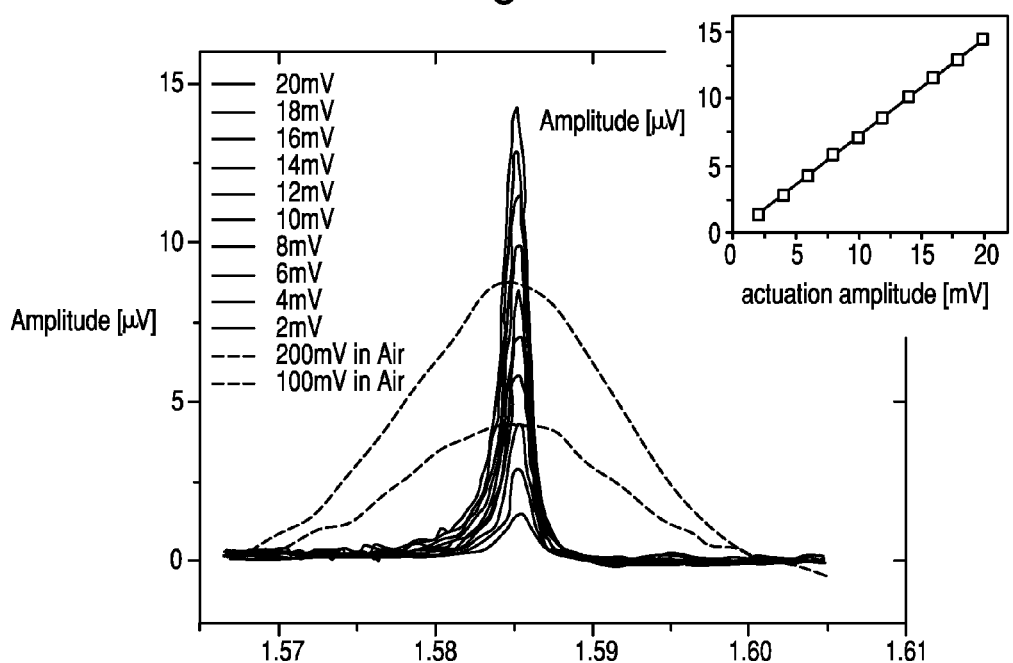
Figure 3:
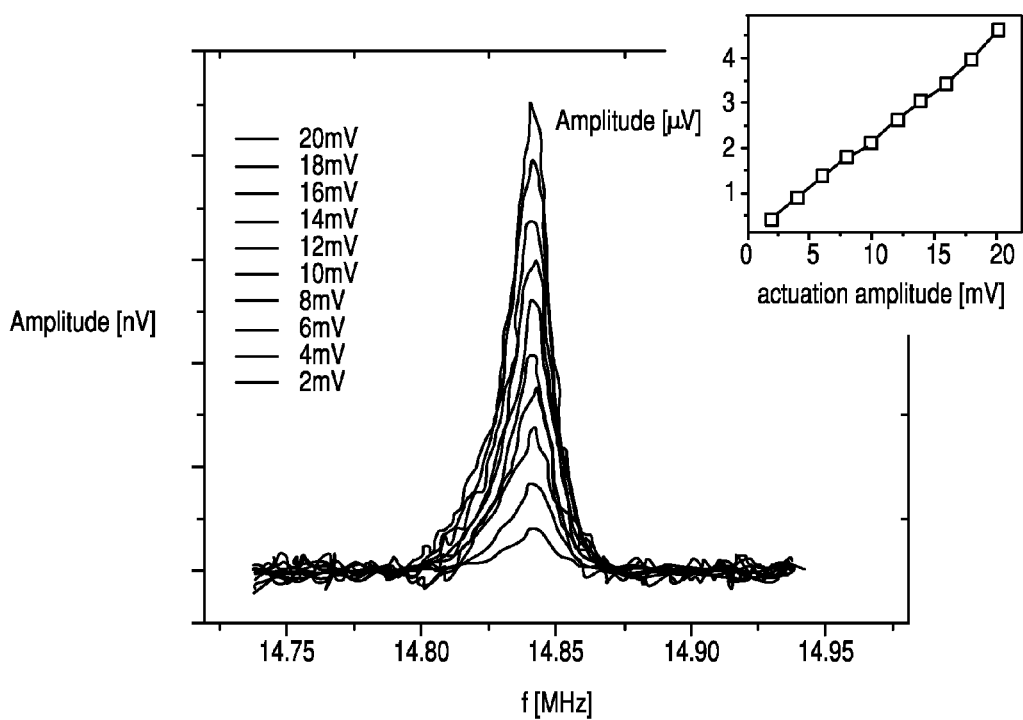

In FIGS. 2 and 3, resonance signals of the device in FIG. 1a are shown, at different actuation levels with a constant dc bias of 50 mV. The cantilever has two 5 μm long and 500 nm wide legs and a 5 μm long and 2 μm wide pad. It has fundamental resonance at 1.5 MHz and second mode at 14.8 MHz. FIG. 2 shows the resonance curve in the fundamental mode and FIG. 3 shows the resonance curve in the second mode. The insets in FIGS. 2 and 3 show the peak amplitude as a function of actuation level or amplitude. In the linear response region, the amplitude at resonance is proportional to the ac signal amplitude applied to a piezoelectric actuator. In fundamental mode, the cantilever has a Q factor of 1000 in vacuum. The cantilever also works in air with a lower Q of 90, as shown by the dashed lines in FIG. 2. The second mode has a quality factor of about 700.

Figure 4:
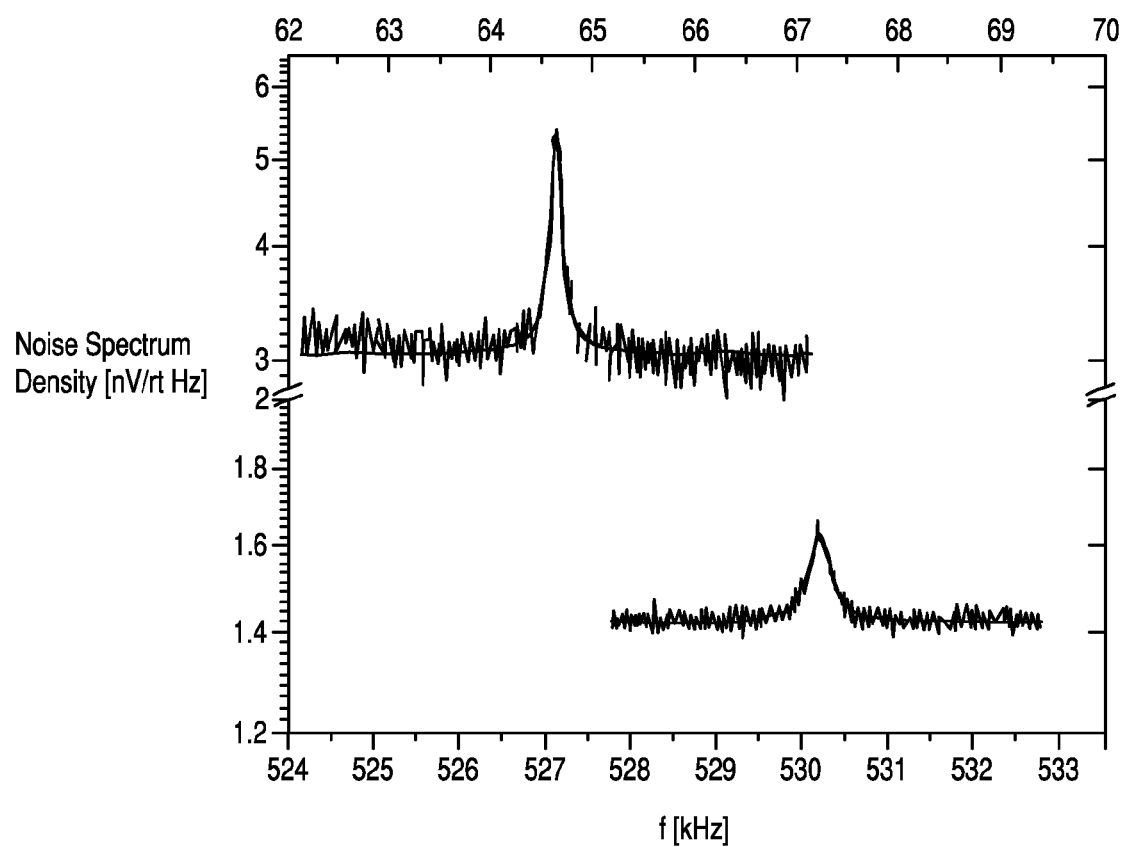
FIG. 4 is a thermomechanical noise spectrum density of the device shown in FIG. 1b. First two modes are shown. Data is fit to Lorentz function.

These piezoresistive cantilevers are sensitive enough to sense their own thermomechanical noise. FIG. 4 displays the noise spectrum of the device shown in FIG. 1b, which has 52 kHz fundamental frequency and second mode at 638 KHz. From the noise spectrum density and using a calculated spring constant, the sensitivity of the cantilever can be calibrated. Apply equipartition principle to cantilever potential energy: $K\langle z^2\rangle = k_b T$ and define sensitivity in static situation as $C_s = \Delta R/R\Delta z$, where K is the spring constant, $k_b$ is Boltzman constant, T is absolute temperature, $\langle z^2\rangle$ is mean square displacement fluctuation of cantilever, $\Delta R/R$ is resistance change ratio of the piezoresistor and $\Delta z$ is the cantilever static displacement. An estimation can be obtained by integrating the noise spectrum density curve to get $\langle v^2\rangle = C_s^2 \langle z^2\rangle$, where $\langle v^2\rangle$ is mean square voltage fluctuation. From the device geometry and elastic properties of SiC and gold, we calculate a spring constant of K≈0.0024N/m. Sensitivity is determined to be $C_s$=1.6×10$^{-7}$/Å. Measurement is limited by Johnson and amplifier noise, with a noise floor of 3 nV/$\sqrt{Hz}$ at 52 KHz and 1.4 nV/$\sqrt{Hz}$ at 638 KHz. The cantilever has a force resolution of 3.8 fN/$\sqrt{Hz}$ at 500 KHz. It is apparent that, although the sensitivity of the device is relatively low, it still has a sufficient resolution due to the low noise floor.

The geometry of the device shown in FIG. 1b may be changed to further improve force resolution or displacement resolution. In the device of FIG. 1b, the strain sensing element 9 only occupies one tenth the length of the cantilever. For a given spring constant, the force sensitivity will be proportional to 1/t$^2$, so making the cantilever thinner and shorter will result in improved force sensitivity. It is noted that doped silicon devices also suffer from large 1/f noise. Hooge's law holds that 1/f noise is inversely proportional to the total carrier number; therefore, making a smaller cantilever will deteriorate noise performance. While in a metal film case, the carrier number (~10$^{22}$/cm$^3$) is four orders of magnitude larger than that in a typical doped semiconductor (~10$^{18}$/cm$^3$). 1/f noise is not a limiting issue.

In addition to cantilevers, thin metal films can also be used in other geometries. Thus, the metal film piezoresistive sensor may be used with other resonators, including, but not limited to, doubly clamped beams, torsional resonators, and diaphragm resonators.

Device Application Examples

Figure 5A:
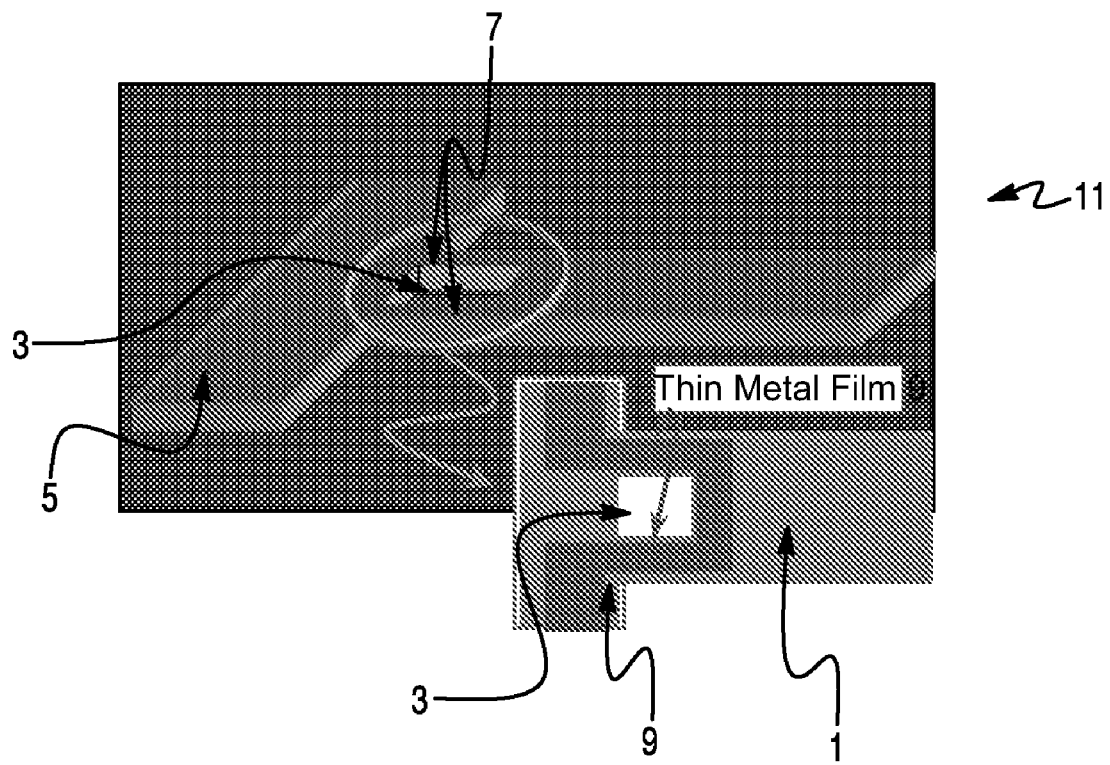
FIG. 5a is a three dimensional schematic view of a device according to embodiments of the invention.
Figure 5B:
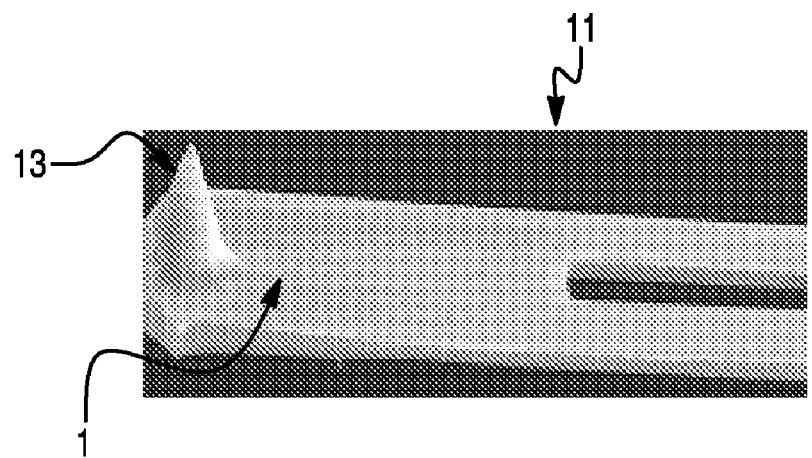
FIG. 5b is an SEM image of an AFM probe according to embodiments of the invention.

FIGS. 5a and 5b illustrate an example of the use of the metal films in self-sensing cantilever probes for atomic force microscopes. FIG. 5a is a schematic and FIG. 5b is an SEM image of a micromachined cantilever (i.e., probe) 11 with the following micro-scale dimensions: 150 μm long×30 μm wide×4 μm thick. The probe 11 contains the cantilever 1, the notch 3, base 5, legs 7, metal film 9 and a sharp AFM tip 13. Preferably, but not necessarily, the metal film 9 is formed on the same side of the cantilever as the tip 13. The specific probe 11 shown in FIG. 5 is designed for tapping-mode AFM. Probes for contact mode AFM can be designed as well, but with much smaller spring constants, as will be described in more detail below.

FIGS. 12 and 13 illustrate the fabrication processes for both non-contact mode probes 11 and contact mode probes 21, respectively. As shown in FIGS. 12a-h, a method for making non-contact/tapping mode piezoresistive SPM probes 11 with thin metal films 9 comprises the following steps.

Figure 12A:
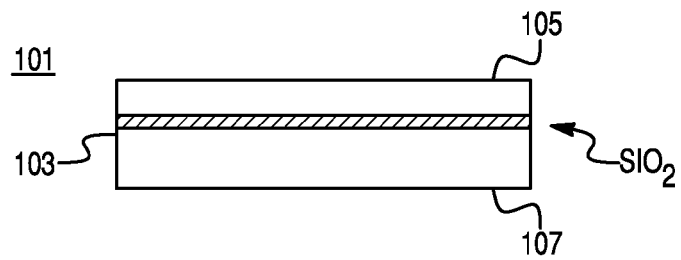
FIGS. 12a-h are side cross sectional views of the steps in the fabrication process flow for self-sensing non-contact/tapping mode piezoresistive SPM probes.

First, as shown in FIG. 12a, a starting substrate 101 is provided. The substrate may be, for example, any suitable SOI (silicon on insulator) substrate, such as a SIMOX (i.e., oxygen implanted) or UNIBOND (i.e., bonded) SOI substrate. The substrate may be 400 to 900 microns, such as 550 microns thick, with a 0.5 to 5 micron thick oxide layer 103 between two silicon portions 105, 107.

Figure 12B:
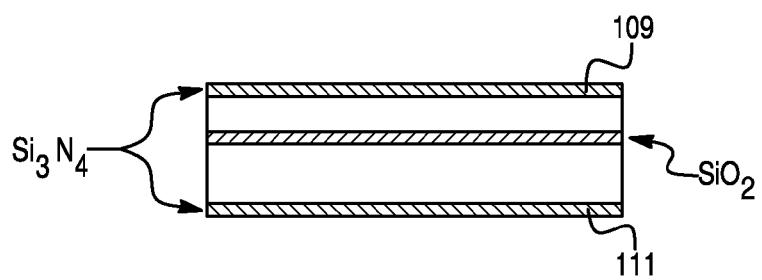

Then, as shown in FIG. 12b, masking layers 109 and 111, which can be made of any material usable as a mask for etching of silicon, are deposited on both sides of the substrate 101. For example, layers 109 and 111 may comprise 400 to 2000 angstrom, such as 550 angstrom thick, LPCVD deposited silicon nitride layers. Other materials, such as silicon oxynitride or aluminum oxide may also be used.

Figure 12C:
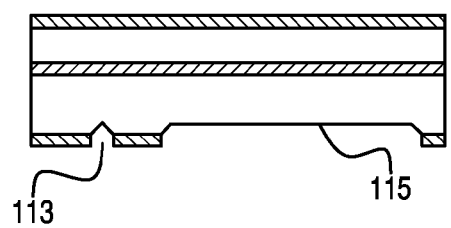

Then, as shown in FIG. 12c, the masking layer 111 is patterned using photolithography (i.e., deposition/spin coating of photoresist on the masking layer, a bake of the photoresist, a selective exposure of the photoresist, patterning of the photoresist and selective etching of the masking layer). Specifically, a crystal axis exposure pit 113 and cantilever area opening 115 are provided in the layer 111 and extend into the silicon portion 107 of the substrate 101. The pit 113 may be formed by a KOH pit etch and the opening 115 may be formed by reactive ion etching of layer 111 using the photoresist mask.

Figure 12D:
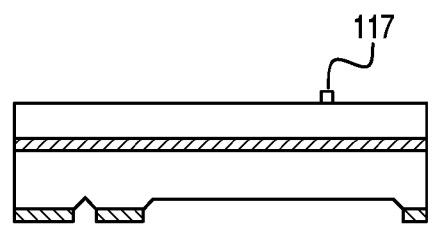

Then, as shown in FIG. 12d, a tip mask is formed. Preferably, the tip mask 117 is formed by photolithographically patterning the masking layer 109 to leave the tip mask 117. For example, portions of layer 109 not covered by a patterned photoresist layer may be reactive ion etched to form the mask 117. Preferably, but not necessarily, the photoresist used in this step is removed prior to the tip etching step.

Figure 12E:
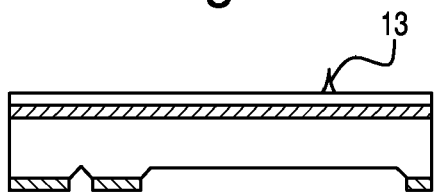

Then, as shown in FIG. 12e, the tip mask 117 is used in the tip etching step. The tip 13 is formed by etching the silicon portion 105 using the tip mask 117. For example, the silicon 105 may be isotropically etched using KOH and be subjected to an oxidation/HF etch cycle to form the tip 13. During this step, the silicon portion 105 of the substrate 101 is thinned such that its thickness is approximately equal to the desired cantilever 1 thickness.

Figure 12F:
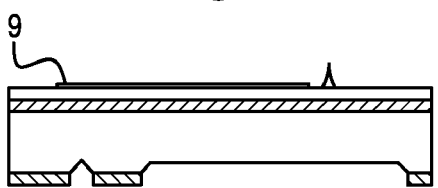

Then, as shown in FIG. 12f, the metal pad and the metal piezoresistive film 9 are formed. Preferably, the metal film, such as a 30 to 70 nm, for example 50 nm thick Au layer is formed on the silicon portion 105 adjacent to the tip 13 (i.e., the metal is preferably formed on the front or tip side of the substrate). The metal pad and film 9 may be patterned into a desired shape using photolithography. Alternatively, the metal pad and layer 9 may be patterned by the lift off method by depositing the metal on a photoresist pattern and then lifting off the photoresist pattern to leave the patterned metal on the silicon portion 105 of the substrate 101.

Figure 12G:
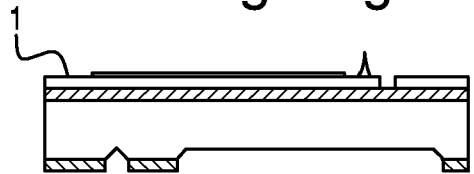

Then, as shown in FIG. 12g, the cantilever 1 is patterned using photolithography. For example, the silicon portion 105 of the substrate may be patterned using RIE or wet etching.

Figure 12H:
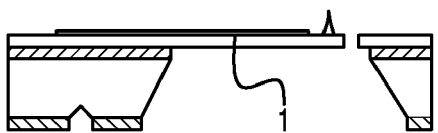

Then, as shown in FIG. 12h, the back side of the substrate 101 is etched to release the cantilever 1. This may be accomplished, for example, by a KOH etch of the back side silicon portion 107 of the substrate through the opening 115 in the masking layer 111, followed by an HF etch to remove the oxide 103 under the cantilever 1.

It should be noted that other materials and etching methods/media may also be used. Furthermore, the photoresist layers may be removed right after the etching step or they may be removed at a later time. For example, the photoresist used to form the opening 115 may be removed right after forming the opening 115 or after the step shown in FIG. 12h.

FIGS. 13a-h illustrate a method of forming a contact mode piezoresistive SPM probe 21. In FIGS. 13a-h, the front side of the probe is shown on bottom rather than the top side of the probe. Of course "top" and "bottom" are relative terms depending on which way the probe is positioned and are used herein only to describe the elements in the figures.

Figure 13A:
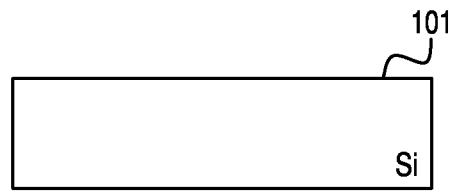
FIGS. 13a-h are side cross sectional views of the steps in the fabrication process flow for self-sensing contact mode piezoresistive SPM probes.

First, as shown in FIG. 13a, a starting substrate 101 is provided. The substrate may be, for example, any suitable semiconductor or insulating substrate, such as a silicon wafer. Thus, an SOI substrate is not necessarily used in this method. The wafer may have the same thickness as the SOI substrate in FIG. 12a.

Figure 13B:
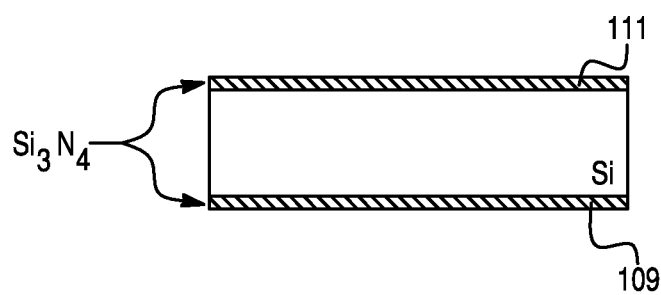

Then, as shown in FIG. 13b, masking layers 109 and 111, which can be made of any material usable as a mask for etching of silicon, are deposited on both sides of the substrate 101. For example, layers 109 and 111 may comprise low stress 800 to 1500 angstrom, such as 1000 angstrom thick, LPCVD deposited silicon nitride layers. Other materials, such as silicon oxynitride or aluminum oxide may also be used.

Figure 13C:
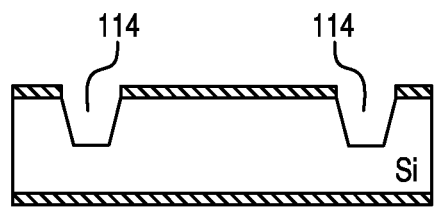

Then, as shown in FIG. 13c, the back side masking layer 111 is patterned using photolithography to form alignment holes 114 extending into the back side of the substrate 101. The holes 114 may be formed by reactive ion etching of layer 111 using a photoresist mask following by a KOH etch of the substrate 101 using the patterned layer 111 and optionally the photoresist (if it has not been removed yet) as a mask. The KOH etch may comprise an etch using 30% KOH solution at 60 degrees Celsius, for example.

Figure 13D:
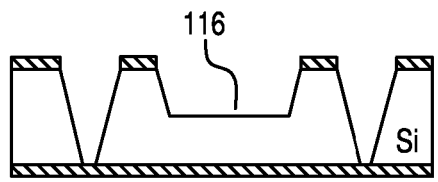

Then, as shown in FIG. 13d, a membrane mask is defined in layer 111. Specifically, a membrane opening 116, which extends into the substrate, is formed in layer 111 using photolithography. The opening 116 may be formed by reactive ion etching of layer 111 using a photoresist mask following by a KOH etch of the substrate 101 using the patterned layer 111 and optionally the photoresist (if it has not been removed yet) as a mask. The KOH etching of the substrate deepens the holes 114 until they extend to the front side masking layer 109.

Figure 13E:
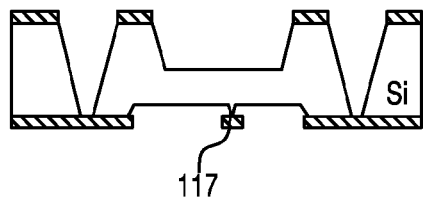

Then, as shown in FIG. 13e, a tip mask is formed. Preferably, the tip mask 117 is formed by photolithographically patterning the masking layer 109 to leave the tip mask 117. For example, portions of layer 109 not covered by a patterned photoresist layer may be reactive ion etched to form the mask 117. Preferably, but not necessarily, the photoresist used in this step is removed prior to the tip etching step. E-beam lithography alignment marks may also be formed during this step.

Figure 13F:
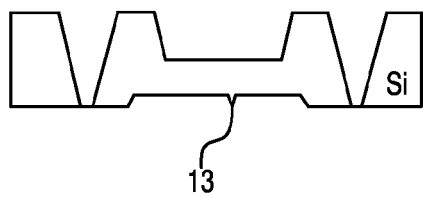

Then, as shown in FIG. 13f, the tip mask 117 is used in the tip etching step. The tip 13 is formed by etching the front side of the substrate using the tip mask 117. For example, the silicon substrate 101 may be isotropically etched using KOH. The remaining masking layer 111 is then preferably removed.

Figure 13G:
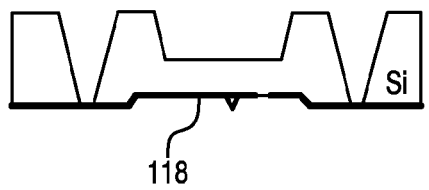

Then, as shown in FIG. 13g, an optional low pressure silicon nitride layer 118 is formed over the front side of the substrate 101 and over the tip 13, such that the tip surface is coated with silicon nitride. Other suitable coating materials may also be used. Then the metal pad and the metal piezoresistive film 9 are preferably formed directly on layer 118 over the front side of the substrate 101. The metal film 9 may be the same as the film 9 shown in FIG. 12f. The metal film 9 may be patterned using any suitable method, such as electron beam lithography, for example.

Figure 13H:
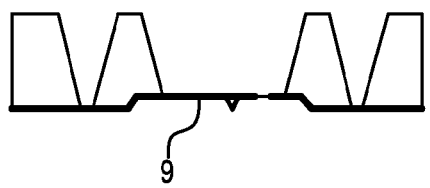

Then, as shown in FIG. 13h, the back side of the substrate 101 is etched to release the cantilever 1. This may be accomplished, for example, by a KOH etch of the back side of the substrate through the opening 116 in the masking layer 111.

It should be noted that other materials and etching methods/media may also be used. Furthermore, the photoresist layers may be removed right after the etching step or they may be removed at a later time.

Thus, a general method of making the probes 11 and 21 comprises providing a substrate; forming masking layers on front and back sides of the substrate; patterning the masking layers; using a patterned masking layer on a front side of the substrate to form an SPM tip in the front side of the substrate; forming a patterned metal film piezoresistive sensor on the front of the substrate; and etching the substrate from the back side through an opening in a back side masking layer to form a cantilever supporting the SPM tip and the metal film.

Piezoresistive Response Example

Figure 6:
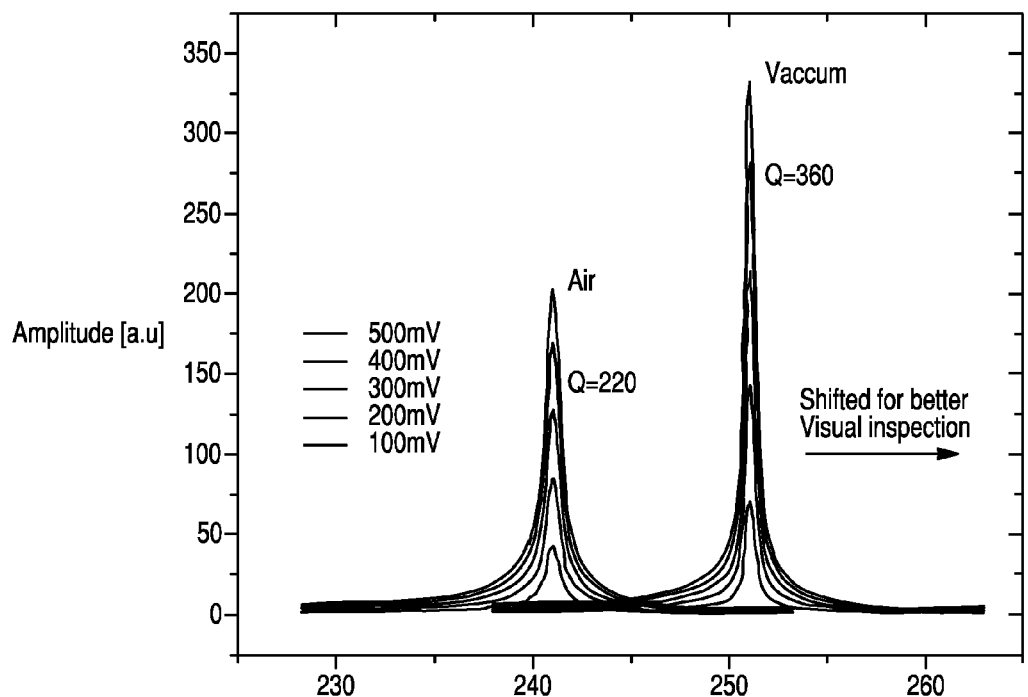
FIGS. 6 and 8 are plots of piezoresistive response of devices of embodiments of the invention.

FIG. 6 illustrates a piezoresistance response of a metal film on the cantilever similar to that in FIG. 5b according to another example of the present invention. The cantilever is 125 microns long, 40 microns wide and 4 microns thick with a conventional tip. The cantilever is suitable for a self-sensing probe 11 designed for tapping mode AFM applications (i.e., this is a larger MEMS device rather than a NEMS device shown in FIG. 1a). A gold thin film covers the two legs of the cantilever and forms a current loop. A very strong piezoresistance response is observed, as shown in FIG. 6. Non-resonant background signal is subtracted from the raw data. The quality factor for this specific cantilever is about 220 in air. Under vacuum conditions, the piezoresistance response is stronger, with quality factor rising above 360. The data for vacuum is shifted to the right for better visual inspection.

Figure 14:
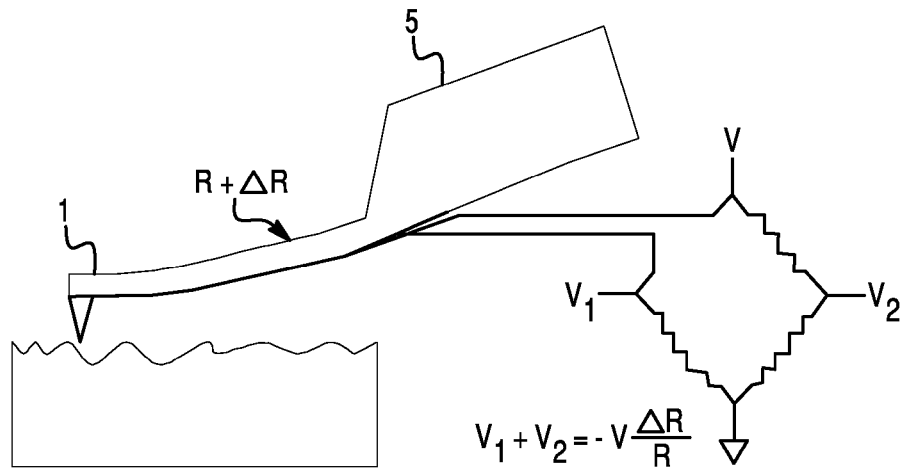
Figure 15:
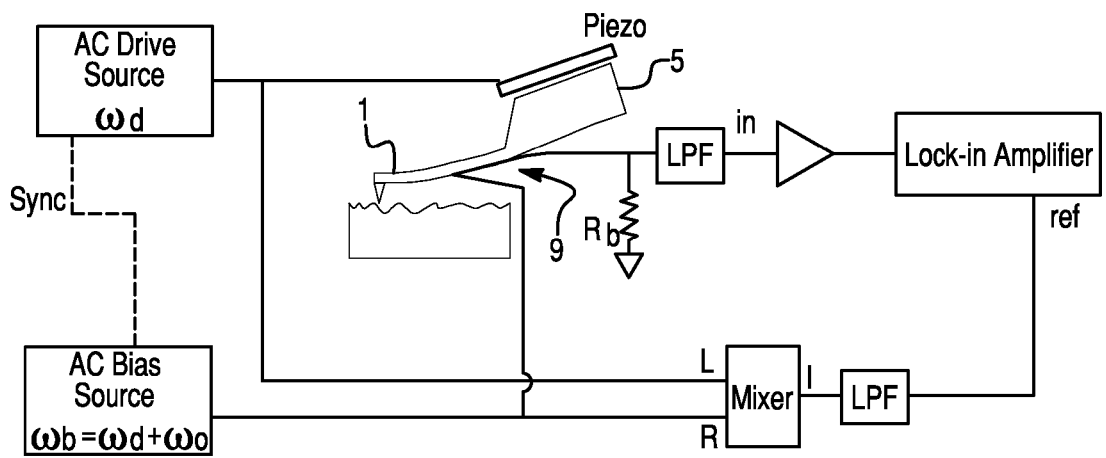

The measurement circuit setup for this experiment is shown in FIGS. 14 and 15. FIG. 14 illustrates a scheme to measure the piezoresistive response of SPM probe when the probe is used in contact mode AFM. In an embodiment shown in FIG. 14, an ac bias current is passed through the piezoresistor and ac voltage is measured to enhance the measurement sensitivity. The scheme in FIG. 14 provides a simple bridge resistance measurement. Furthermore, DC measurement can be directly employed to detect the bending of the cantilever. Lock-in at fixed frequency (e.g. 20 kHz) can be employed to enhance the measurement sensitivity.

FIG. 15 illustrates a scheme to measure the piezoresistive response of SPM probe when the probe is used in tapping/non-contact/ac mode AFM. The bias current through piezoresistor is modulated at one frequency, while the cantilever is driven at another, different frequency. The mechanical response of the cantilever is detected at their difference frequency or their sum frequency.

Thus, as shown in FIG. 15, an ac drive source is used to drive the cantilever 1 through a piezo drive source in the base 5. The drive source is synchronized with an ac bias source and the outputs of the ac drive and bias sources are provided into different inputs of the mixer. The output of the mixer is provided through a low pass filter (LPF) into a lock-in amplifier as a reference signal. The ac bias source is used to bias the metal film 9, whose output is also provided into the lock-in amplifier through another LPF and amplifier. In the scheme of FIG. 15, the ac drive source can be used to drive the cantilever at resonant frequency, such as 240 kHz for example. Direct lock-in measurement can be employed to detect the amplitude of the oscillation. To remove the electrical background due to crosstalk, example shown above employs a down-mix detection scheme, which will be described in more detail below. The sample bias current may be applied at resonant frequency that is 10-50 kHz higher, such as 20 kHz higher than the drive frequency (e.g. 260 kHz for a 240 kHz drive frequency). Lock in measurement is performed at 20 kHz or 500 kHz, for example (see provisional application Ser. No. 60/562,652, incorporated by reference for additional details).

Figure 7:
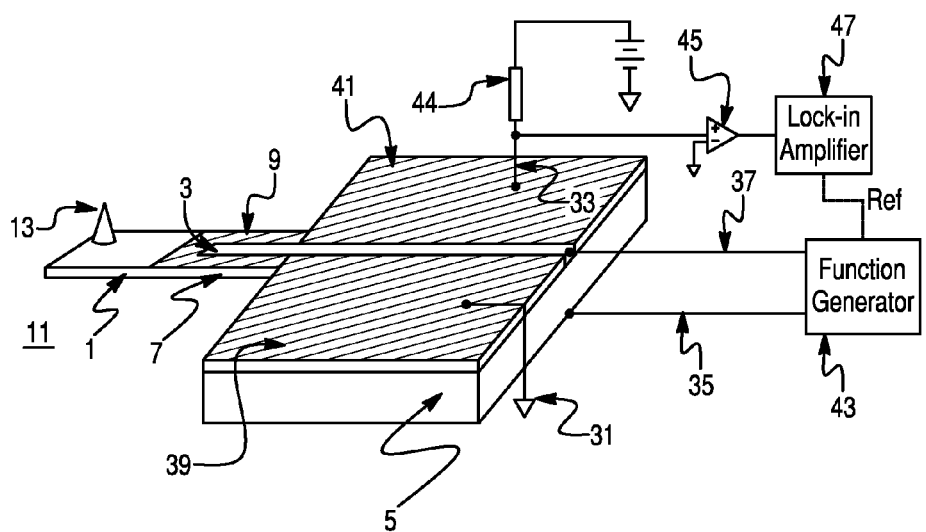
FIGS. 7, 14 and 15 are schematics of testing set ups used to test the devices of the examples of the present invention.

The probe 11 is then tested with a commercial AFM system (DI dimension 3100 system) equipped with a signal access module for external signal access and control. The measurement set up is illustrated schematically in FIG. 7. The standard DI probe holder is modified to facilitate the testing of the metallic piezoresistive probes. First, the electrical connections from the chip holder to the AFM headstage are disconnected. Second, four wires 31, 33, 35, 37 are soldered to the chip holder to enable an electrical connection to the piezo actuator 5 under the probe 11 and connections to two electrical contacts pads 39, 41 on the self-sensing probe. The drive signal is applied to piezo actuator 5 through an external function generator 43 (Stanford Research System DS345). A dc bias voltage is supplied across the two legs 7 of the cantilever 1. A resistor 43 with a resistance value similar to that of the cantilever is used as a balance resistor (20.3 Ohms) for extraction of resonant ac signal. The voltage change across the probe 11 is further amplified through a low-noise voltage amplifier 45 (Stanford Research System SR560). This oscillating ac voltage is then fed into a lock-in amplifier 47 (Stanford Research System SR830). The measurement is locked into the drive signal provided by the function generator. x-output of the lock-in amplifier is supplied to one input channel of the nanoscope controller through signal access module after the phase extender box.

Figure 8:
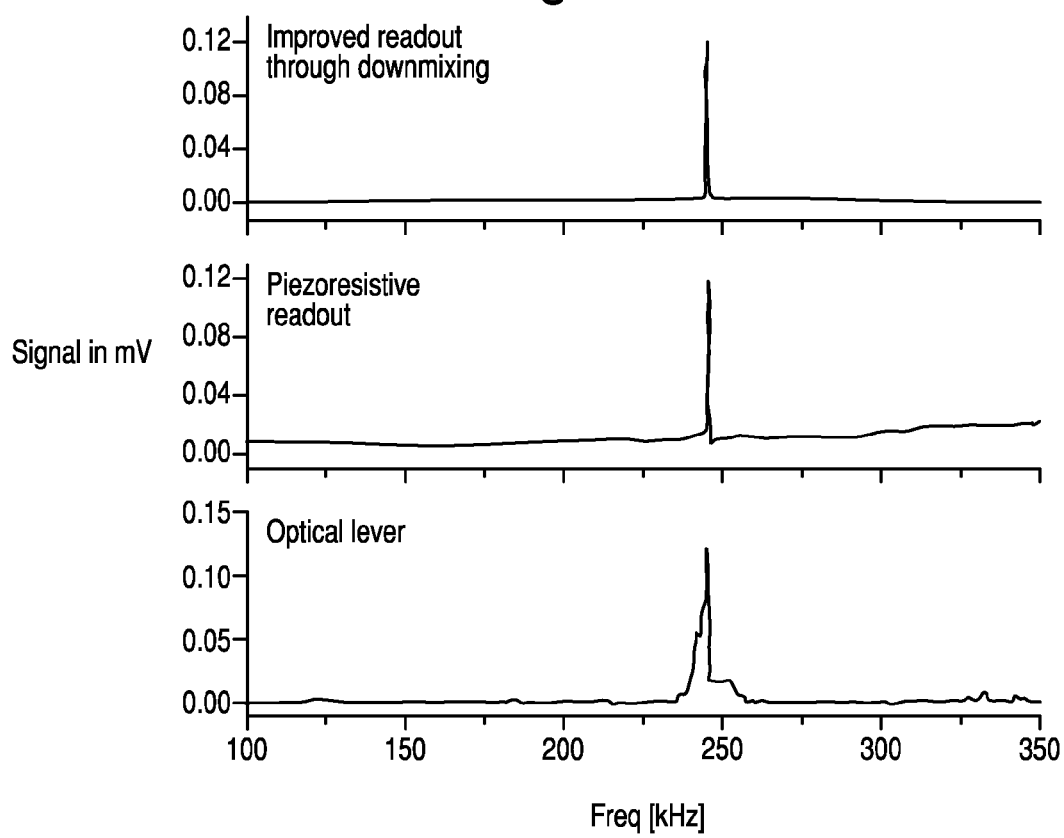

Resonant curves from electrical measurement are first obtained. FIG. 8 shows three resonant curves from the same cantilever. Trace 1 (bottom curve) is the result from AFM built-in laser deflection measurement. Trace 2 (middle curve) is a direct electrical lock-in measurement of the cantilever with dc bias current. Trace 3 (upper curve) is an improved measurement result with ac bias current (down mix scheme described above). Comparable signal strengths are observed in all three curves. In optical data, side bands due to non-flexural resonance are apparent. They are absent in the electrical measurement curves. Apparently electrical measurements are immune to the shear motion displayed in the optical measurement data. A comparison between trace 2 and trace 3 shows that the down mix scheme can effectively eliminate the cross-talk signal that is usually inevitable in such a measurement.

Figure 9:
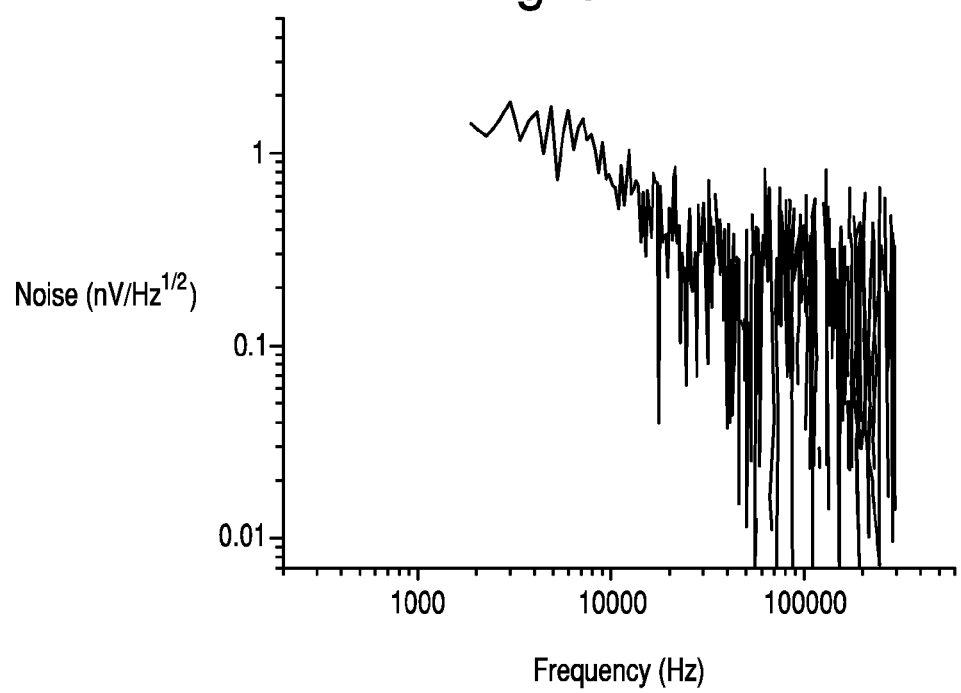
FIG. 9 is a plot of a noise spectrum from a metallic thin film piezoresistor.

The noise spectrum measurement is then performed on the metallic thin film probe, as shown in FIG. 9. Very low noise spectrum is observed. For frequency >1000 Hz, the noise level is below 1 nV/$\sqrt{Hz}$, smaller than the Johnson noise generated by a 50 Ohm resistor at room temperature. Generally speaking, at the same frequency range, the noise level in p+ silicon is about 30 nV/√Hz. The noise performance of metallic piezoresistor is at least about 30 times better than semiconducting Si material.

Figure 10:
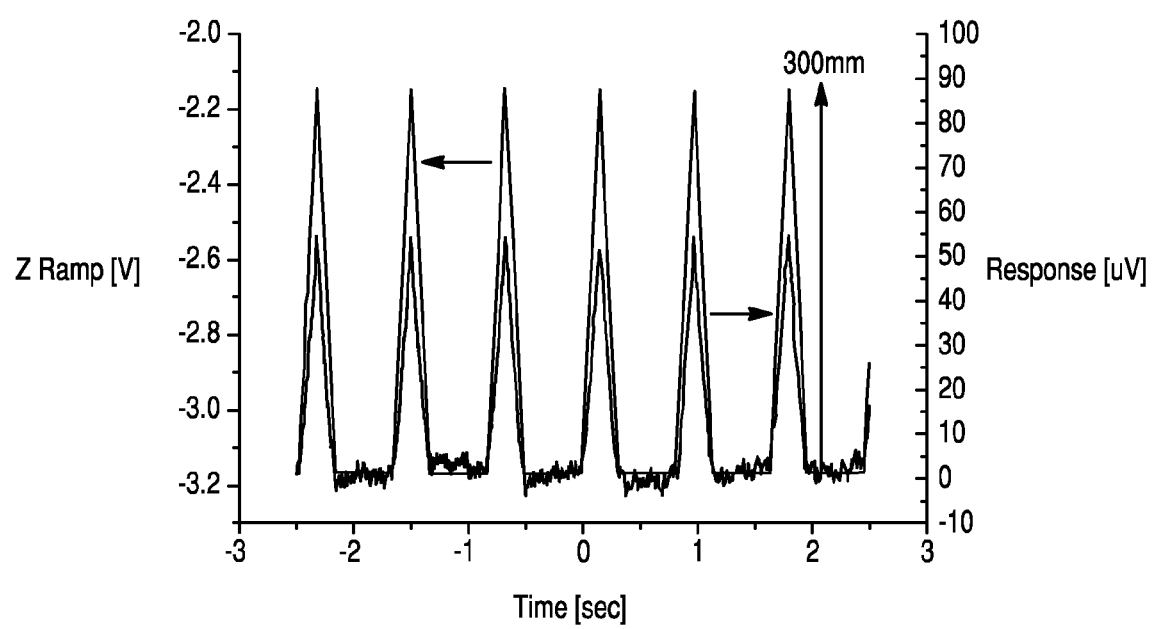
FIG. 10 is a plot of force indentation of piezoresistive probes.

For contact-mode AFM, the cantilever is not operated at resonance but follows the topography of the sample surface. Cantilever's DC or quasi-DC response is of most concern for contact-mode operations. In this case, AFM force indentation is employed to modulate the piezo probe z motion at a certain range after the cantilever is in contact with sample surface. The cantilever is bent accordingly at the modulation frequency. The modulated piezoresistive signal is picked up by a wide-band dc amplifier and measured by an oscilloscope. Data for force indentation of the probes is shown in FIG. 10 (right axis). The voltage applied to z-component of the piezo-tube is also shown for comparison (left axis). This voltage modulation corresponds to 300 nm bending amplitude. 55 µV signal amplitude is observed across the piezoresistive probe. This corresponds to 0.88 mV/nm after 2000 times voltage amplification. For standard optical AFM detection, the response is 20 mV/nm. Given the extremely low noise in the exemplary piezoresistor, a 30 times higher gain amplifier can be used and work on comparable noise floor with a signal response of 26.4 mV/nm, matching the performance of the optical cantilevers.

Figure 11A:
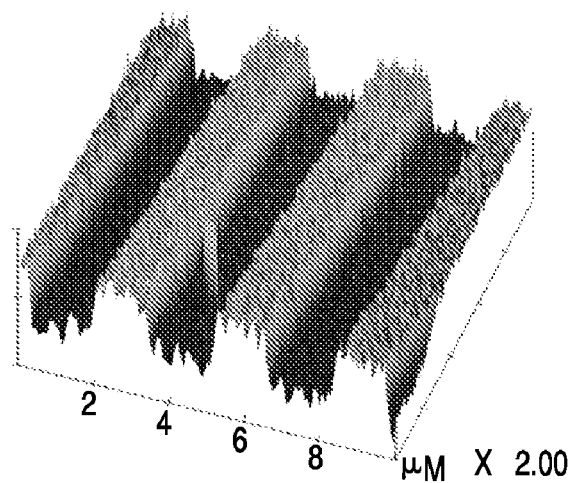
FIG. 11a is a 3D topographical image obtained from direct tapping mode. AFM.
Figure 11B:
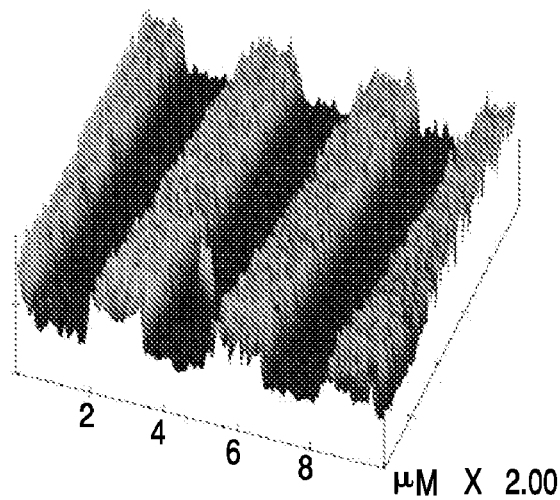
FIG. 11b is a 3D topographical image obtained from lock-in measurement of the metallic thin film piezoresistor.

A standard SPM calibration grating is employed to demonstrate the imaging capability of the exemplary metallic thin film probes. The grating is a 1-D array of rectangular $SiO_2$ steps on a silicon wafer with 3 micron pitch. The step height is 20 nm±1 nm. The topographic image shown in FIG. 11b is acquired from monitoring the output of the lock-in amplifier when AFM is operated at "lift mode". Optical tapping mode AFM image is present in FIG. 11a for comparison. Even without signal conditioning, the metallic thin-film piezoresistor yields very high signal to noise ratio. The image quality is comparable to that of the optical measurement result. Thus, the SPM, such as the AFM is used to either determine and/or image characteristics of a surface being examined by the AFM probe 11, 21 based on the piezoresistive response of the metal film 9. In other words, the AFM probe may be used to image a surface of a material as shown in FIG. 11b or to determine one or more characteristics of the surface of a material, as may be carried out with an AFM. Furthermore, while not shown in the Figures, a data processing device, such as a computer or a dedicated processor, is used to process the signal from the AFM probe and the associated equipment, such as the lock-in amplifier, to create, store and/or display the image and/or data corresponding to the surface characteristics. A metal film has been described above as the preferred piezoresistive film. However, other piezoresistive material films may also be used instead. For example, piezoresistive semiconductor films, such as doped silicon films, for example p-type doped silicon films, may be formed on resonator surfaces and used to detect movement of the resonator.

The foregoing description of the invention has been presented for purposes of illustration and description. It is not intended to be exhaustive or to limit the invention to the precise form disclosed, and modifications and variations are possible in light of the above teachings or may be acquired from practice of the invention. The description was chosen in order to explain the principles of the invention and its practical application. It is intended that the scope of the invention be defined by the claims appended hereto, and their equivalents.

The invention claimed is:

1. A microelectromechanical or nanoelectromechanical system comprising a) a movable element having a size from 1 nm to less than micron in at least one dimension; and b) a piezoresistive sensing element configured to sense a movement of the movable element, said piezoresistive sensing element comprising a thin metal film, wherein, when the movable element moves in a first direction, at least a portion of the thin metal film extends in the first direction.

2. The system of claim 1, wherein the movable element has a size of no more than 100 microns in at least two of the three dimensions.

3. The system of claim 1, wherein the movable element is a cantilever.

4. The system of claim 1, wherein the thin metal film has a thickness from 10 nm to 10 microns.

5. The system of claim 1, wherein the thin metal film is a wire having a cross sectional area of about 100 $nm^2$ or less.

6. The system of claim 1, wherein the thin metal film is a discontinuous metal film.

7. The system of claim 1, wherein the thin metal film comprises at least one of Au, W, Pt, Al, Cu, Cr, Ag, Pd and Ni.

8. The system of claim 1, wherein the thin metal film comprises a metal alloy.

9. The system of claim 8, wherein the metal alloy is Constantan, Karma, Isoelastic, Niclirome V, Pt—W or Pd—Cr alloy.

10. The system of claim 1, wherein the piezoresistive sensing element has a noise level below 3.5 nV/√Hz in a frequency range 62 kHz-67 kHz or a noise level below 1.0 nV/√Hz at a frequency of 5000 kHz.

11. The system of claim 1, further comprising a current source configured to provide a current across the thin metal film and a detector configured to detect a voltage across the thin metal film to determine an amount of the movement of the movable element.

12. A microelectromechanical or nanoelectromechanical system comprising a) a movable element; and b) a piezoresistive sensing element configured to sense a movement of the movable element, said piezoresistive sensing element comprising a thin metal film, wherein the piezoresistive sensing element has a noise level in a frequency range 62 kHz-67 kHz below 3.5 nV/√Hz or a noise level at a frequency of 5000 kHz below 1.0 nV/√Hz.

13. The system of claim 12, wherein the movable element has a size of no more than 100 microns in at least two of the three dimensions.

14. The system of claim 12, wherein the movable element has a size from 1 nm to less than micron in at least one dimension.

15. The system of claim 12, wherein the movable element is a cantilever.

16. The system of claim 12, wherein the thin metal film covers at least a portion of a surface of the movable element.

17. The system of claim 12, wherein the thin metal film is a gold film.

18. The system of claim 17 wherein the gold film has a thickness from 30 nm to 10 microns.

19. The system of claim 12, further comprising a current source configured to provide a current across the thin metal film and a detector configured to detect a voltage across the thin metal film to determine an amount of the movement of the movable element.

20. A method of operating a microelectromechanical or nanoelectromechanical system comprising a movable element and a metal film piezoresistive sensing element, the method comprising:
  operating the movable element at a frequency of 62 kHz-67 kHz or 5000-100,000 kHz; and
  determining an amount of the movement of the movable element;
  wherein the piezoresistive sensing element has a noise level in the frequency range 62 kHz-67 kHz below 3.5 nV/$\sqrt{Hz}$ or a noise level in the frequency of 5000-100,000 kHz below 1.0 nV/$\sqrt{Hz}$.

* * * * *